US00PP24785P2

(12) United States Plant Patent
Verschoor

(10) Patent No.: US PP24,785 P2
(45) Date of Patent: Aug. 19, 2014

(54) ***VERONICA* PLANT NAMED 'VERSPINK'**

(50) Latin Name: *Veronica spicata*
Varietal Denomination: Verspink

(71) Applicant: Janus Verschoor, Haarlem (NL)

(72) Inventor: Janus Verschoor, Haarlem (NL)

( * ) Notice: Subject to any disclaimer, the term of this patent is extended or adjusted under 35 U.S.C. 154(b) by 0 days.

(21) Appl. No.: 13/694,814

(22) Filed: Jan. 7, 2013

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Anne Grunberg
(74) *Attorney, Agent, or Firm* — C. A. Whealy

(57) ABSTRACT

A new and distinct cultivar of *Veronica* plant named 'Verspink', characterized by its compact and broadly upright plant habit; freely branching habit; dense and bushy appearance; strong flowering stems; freely flowering habit; long flowering period; dense inflorescences with numerous light red purple-colored flowers; and good garden performance.

2 Drawing Sheets

Botanical designation: *Veronica spicata.*
Cultivar denomination: 'VERSPINK'.

BACKGROUND OF THE INVENTION

The present invention relates to a new and distinct cultivar of *Veronica* plant, botanically known as *Veronica spicata* and hereinafter referred to by the name 'Verspink'.

The new *Veronica* plant is a product of a planned breeding program conducted by the Inventor in Haarlem, The Netherlands. The objective of the breeding program was to create new compact and freely-flowering *Veronica* plants with large inflorescences with attractive flowers.

The new *Veronica* plant originated from a cross-pollination made by the Inventor in 2008 in Haarlem, The Netherlands of two unnamed seedling selections of *Veronica spicata*, not patented. The new *Veronica* plant was discovered and selected by the Inventor as a single flowering plant from within the progeny of the stated cross-pollination in a controlled greenhouse environment in Haarlem, The Netherlands in 2010.

Asexual reproduction of the new *Veronica* plant by cuttings in a controlled environment in Haarlem, The Netherlands since 2010 has shown that the unique features of this new *Veronica* plant are stable and reproduced true to type in successive generations.

SUMMARY OF THE INVENTION

Plants of the new *Veronica* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Verspink'. These characteristics in combination distinguish 'Verspink' as a new and distinct *Veronica* plant:

1. Compact and broadly upright plant habit.
2. Freely branching habit; dense and bushy appearance.
3. Strong flowering stems.

4. Freely flowering habit.
5. Long flowering period.
6. Dense inflorescences with numerous light red purple-colored flowers.
7. Good garden performance.

Plants of the new *Veronica* differ primarily from plants of the parent selections in the following characteristics:

1. Plants of the new *Veronica* are more compact than plants of the parent selections.
2. Plants of the new *Veronica* have stronger flowering stems than plants of the parent selections.
3. Plants of the new *Veronica* are more freely flowering than plants of the parent selections.

Plants of the new *Veronica* can be compared to plants of *Veronica spicata* 'Heidekind', not patented. In side-by-side comparisons, plants of the new *Veronica* differed primarily from plants of 'Heidekind' in the following characteristics:

1. Plants of the new *Veronica* were more compact than plants of 'Heidekind'.
2. Plants of the new *Veronica* had stronger flowering stems than plants of 'Heidekind'.
3. Plants of the new *Veronica* were more freely flowering than plants of 'Heidekind'.
4. Plants of the new *Veronica* flowered for a longer period of time than plants of 'Heidekind'.
5. Plants of the new *Veronica* and 'Heidekind' differ in flower color as plants of 'Heidekind' had wine red-colored flowers.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Verspink' grown in an outdoor nursery.

The photograph on the second sheet is a close-up view of a typical flowering plant of 'Verspink'.

DETAILED BOTANICAL DESCRIPTION

Plants used for the aforementioned photographs and following description were grown in during the late summer/early autumn in an outdoor nursery in Haarlem, The Netherlands and under cultural practices typical of commercial production. During the production of the plants, day temperatures ranged from 16° C. to 32° C. and night temperatures ranged from 6° C. to 18° C. Plants were two years old when the photographs and the description were taken. In the following description, color references are made to The Royal Horticultural Society Colour Chart, 2007 Edition, except where general terms of ordinary dictionary significance are used.

Botanical classification: *Veronica spicata* 'Verspink'.

Parentage:

*Female, or seed, parent*.—Unnamed seedling selection of *Veronica spicata*, not patented.

*Male, or pollen, parent*.—Unnamed seedling selection of *Veronica spicata*, not patented.

Propagation:

*Type*.—By cuttings.

*Time to initiate roots, summer*.—About three weeks at temperatures about 20° C.

*Time to produce a rooted young plant, summer*.—About six weeks at temperatures about 20° C.

*Root description*.—Fine, fibrous; white in color.

*Rooting habit*.—Freely branching; medium density.

Plant description:

*Plant type*.—Herbaceous perennial.

*Plant and growth habit*.—Compact and broadly upright plant habit, broad inverted triangle; freely basal branching habit with about 16 lateral branches; low to moderately vigorous growth habit.

*Plant height*.—About 32.5 cm.

*Plant width*.—About 25 cm.

*Lateral branch description*.—Length: About 14.5 cm. Diameter: About 2 mm. Internode length: About 2.1 cm. Strength: Strong. Texture: Densely pubescent. Color: Close to 138B to 138C; older stems, close to N186C.

Foliage description:

*Arrangement*.—Opposite, simple.

*Length*.—About 4.5 cm.

*Width*.—About 1.5 cm.

*Shape*.—Narrowly ovate to elliptic.

*Apex*.—Obtuse to bluntly acute.

*Base*.—Attenuate.

*Margin*.—Crenate to serrate.

*Texture, upper and lower surfaces*.—Sparsely pubescent.

*Venation pattern*.—Pinnate.

*Color*.—Developing leaves, upper surface: Close to 143A. Developing leaves, lower surface: Close to 143C. Fully expanded leaves, upper surface: Close to N137A to N137B; venation, close to 144A to 144B. Fully expanded leaves, lower surface: Close to 147B; venation, close to 144B.

*Petiole length*.—About 1.7 cm.

*Petiole diameter and height*.—About 2 mm by 1.5 mm.

*Petiole texture, upper and lower surfaces*.—Smooth, glabrous.

*Petiole color, upper and lower surfaces*.—Close to 144A.

Flower description:

*Flower shape and arrangement*.—Single campanulate flowers arranged on upright terminal racemes; racemes dense; flowers face outwardly.

*Flowering habit*.—Freely flowering habit with about 120 flowers per raceme.

*Fragrance*.—None detected.

*Natural flowering season*.—Plants begin flowering about 60 to 70 days after planting; long flowering period, in the garden, plants flower continuously from late June to early September in The Netherlands.

*Flower longevity on the plant*.—Individual flowers last about one week; flowers not persistent.

*Flower buds*.—Length: About 5 mm. Diameter: About 2.5 mm. Shape: Ovoid. Color: Close to 63B.

*Inflorescence height*.—About 13.9 cm.

*Inflorescence diameter*.—About 2 cm.

*Flower diameter*.—About 7.5 mm.

*Flower height*.—About 8 mm.

*Petals*.—Quantity and arrangement: Four in a single whorl, petals fused towards the base. Length: About 7 mm. Width: About 2.5 mm. Shape: Oblanceolate. Apex: Broadly acute. Margin: Entire. Texture, upper and lower surfaces: Smooth, glabrous. Color: When opening, upper and lower surfaces: Close to 63A. Fully opened, upper and lower surfaces: Between 63A and 64B; color becoming closer to 64B to 64C with development.

*Sepals*.—Quantity and arrangement: Four in a single whorl, sepals fused towards the base. Length: About 3 mm. Width: About 0.75 mm. Shape: Narrowly ovate. Apex: Acute. Margin: Entire. Texture, upper and lower surfaces: Smooth, glabrous. Color: When opening, upper and lower surfaces: Close to 137B. Fully opened, upper and lower surfaces: Close to 137B.

*Peduncles*.—Length: About 13.4 cm. Diameter: About 2.5 mm. Aspect: Primary racemes, erect; secondary racemes, about 20° from vertical. Strength: Strong. Texture: Smooth, glabrous. Color: Close to 138B to 138C.

*Pedicels*.—Length: About 1 mm. Diameter: About 0.5 mm. Aspect: About 60° from peduncle axis. Strength: Strong. Texture: Smooth, glabrous. Color: Close to 138B.

*Reproductive organs*.—Stamens: Quantity per flower: Two. Filament length: About 5.5 mm. Filament color: Close to 63B to 63C. Anther length: About 1 mm. Anther shape: Elliptic, dorsifixed. Anther color: Close to 64A. Pollen amount: Scarce. Color: Close to 11D. Pistils: Quantity per flower: One. Pistil length: About 7.5 mm. Style length: About 7 mm. Style color: Close to 72D. Stigma shape: Clavate. Stigma color: Close to 72A. Ovary color: Close to 144B.

*Fruits*.—Length: About 3 mm. Diameter: About 2.5 mm. Texture: Pubescent. Color: Close to 200C to 200D.

*Seeds*.—Quantity per fruit: About 24. Length: About 0.75 mm. Diameter: About 0.75 mm. Texture: Smooth, glabrous. Color: Close to N200A.

Disease & pest resistance: Plants of the new *Veronica* have not been noted to be resistant to pathogens and pests common to *Veronica* plants.

Garden performance: Plants of the new *Veronica* have been observed to have good garden performance, to tolerate wind, rain, high temperatures about 35° C. and to be cold hardy to USDA Hardiness Zone 4.

It is claimed:

1. A new and distinct *Veronica* plant named 'Verspink' as illustrated and described.

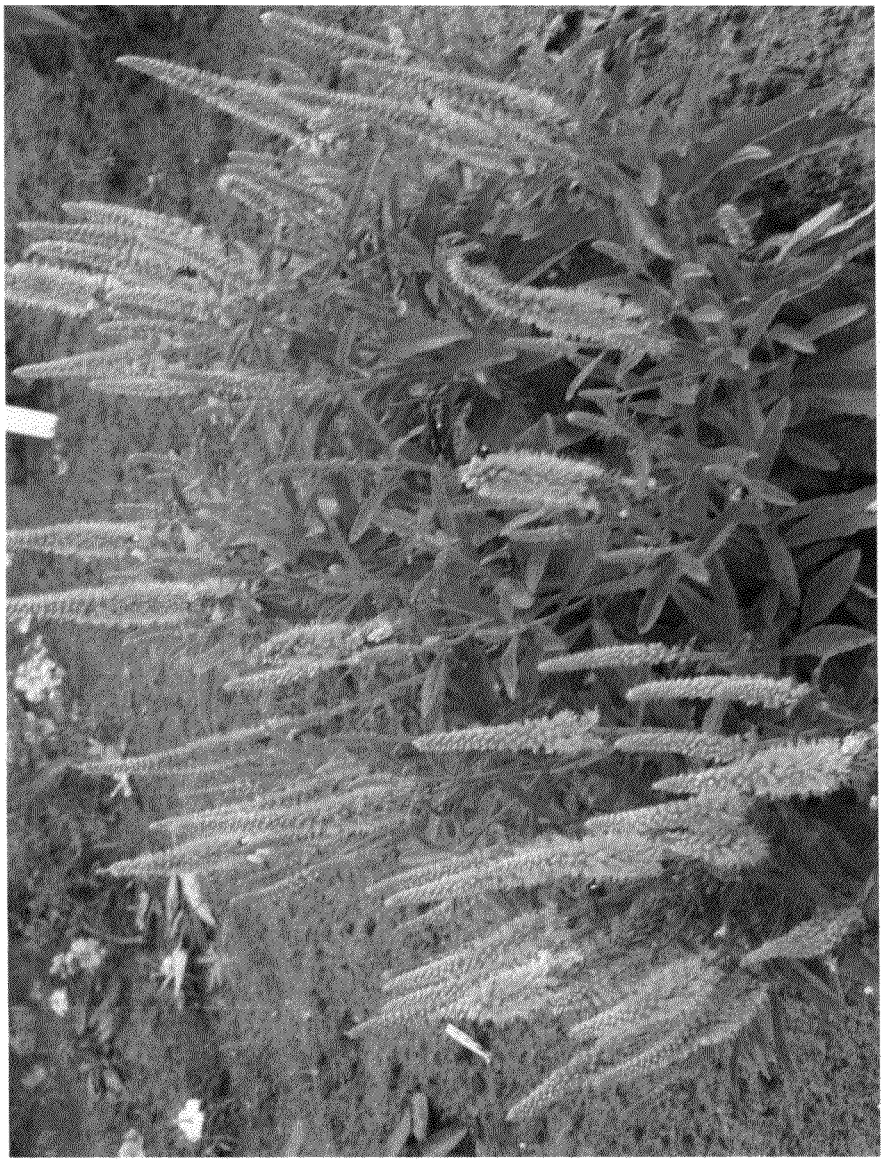

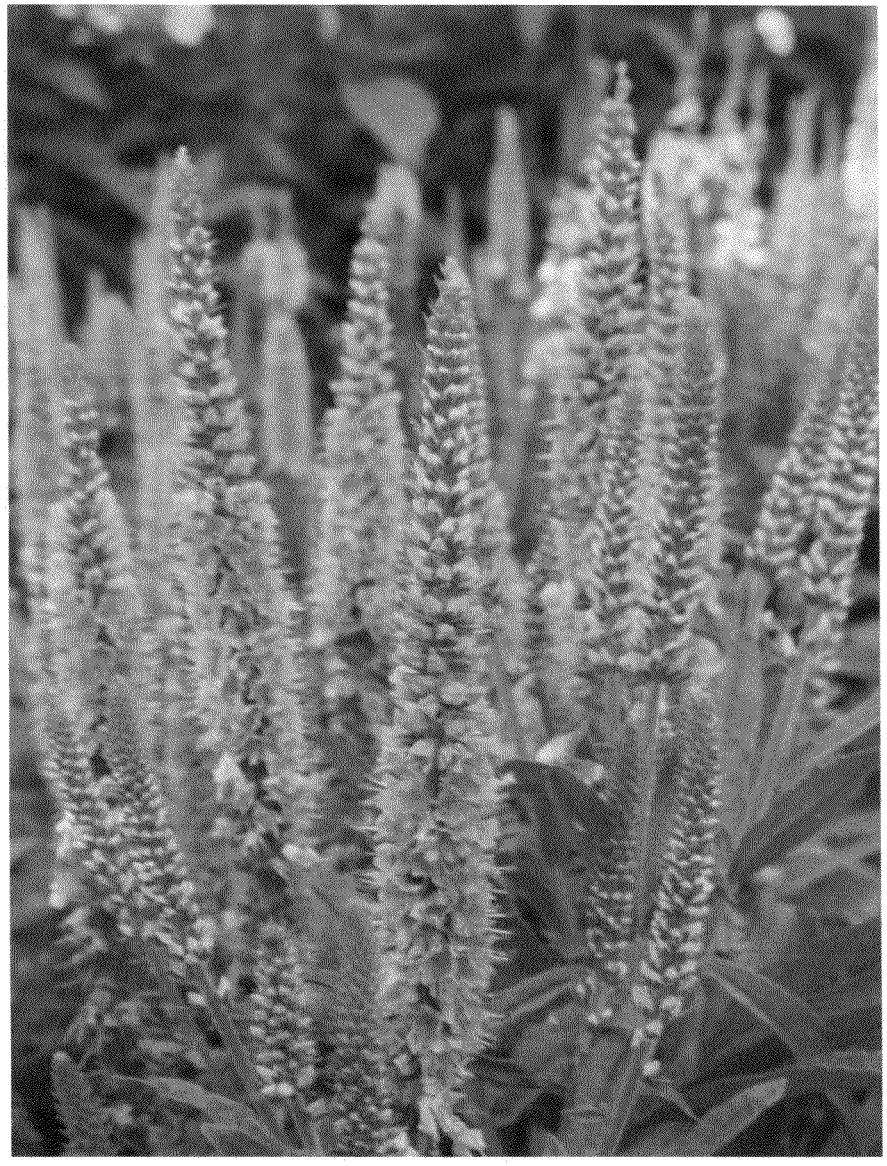

* * * * *